United States Patent [19]
Raad et al.

[11] Patent Number: 5,409,467
[45] Date of Patent: Apr. 25, 1995

[54] ANTIMICROBIAL CATHETER

[75] Inventors: Issam I. Raad, Houston; Gerald P. Bodey, The Woodlands; Alfonso Zermeno, Houston, all of Tex.

[73] Assignee: Board of Regents, The University of Texas System, Austin, Tex.

[21] Appl. No.: 174,223

[22] Filed: Dec. 28, 1993

Related U.S. Application Data

[63] Continuation-in-part of Ser. No. 956,642, Oct. 2, 1992, Pat. No. 5,324,275.

[51] Int. Cl.$^6$ .............................................. A61M 5/32
[52] U.S. Cl. ..................................... 604/265; 604/21
[58] Field of Search ................. 604/265, 266, 280, 20, 604/21; 607/115, 116, 121, 122, 127

[56] References Cited

U.S. PATENT DOCUMENTS

| | | | |
|---|---|---|---|
| 3,543,761 | 12/1970 | Bradley | 128/421 |
| 3,760,812 | 9/1973 | Timm et al. | 607/116 |
| 3,769,984 | 11/1973 | Muench | 128/404 |
| 3,942,536 | 3/1976 | Mirowski et al. | 128/419 |
| 4,054,139 | 10/1977 | Crossley | 128/260 |
| 4,411,648 | 10/1983 | Davis et al. | 604/21 |
| 4,564,361 | 1/1986 | Akiyama | 604/265 |
| 4,569,673 | 2/1986 | Tesi | 604/20 |
| 4,682,596 | 7/1987 | Bales et al. | 128/303.14 |
| 4,723,946 | 2/1988 | Kay | 604/267 |
| 4,764,164 | 8/1988 | Sasaki | 604/20 |
| 4,776,334 | 10/1988 | Prionas | 128/303.1 |
| 4,817,608 | 4/1989 | Shapland et al. | 128/419 |
| 4,832,048 | 5/1989 | Cohen | 128/786 |
| 4,847,049 | 7/1989 | Yamamoto | 422/241 |
| 4,886,505 | 12/1989 | Haynes et al. | 604/265 |
| 4,906,238 | 3/1990 | Greenfeld et al. | 604/266 |
| 4,973,320 | 11/1990 | Brenner et al. | 604/265 |
| 5,002,792 | 3/1991 | Vegoe | 427/2 |
| 5,037,380 | 8/1991 | Jacobsen et al. | 604/20 |
| 5,071,407 | 12/1991 | Termin et al. | 604/104 |
| 5,087,240 | 2/1992 | Sibalis | 604/20 |
| 5,143,071 | 9/1992 | Keusch et al. | 128/640 |
| 5,147,291 | 9/1992 | Cukier | 604/20 |
| 5,213,097 | 5/1993 | Zeindler | 128/401 |

OTHER PUBLICATIONS

Spadaro et al., "Antibacterial Effects of Silver Electrodes with Weak Direct Current," 6 *Antimicrobial Agents and Chemotherapy* 637–642, Nov. 1974.

Berger et al., "Electrically Generated Silver Ions: Quantitative Effects on Bacterial and Mammalian Cells," 9 *Antimicrobial Agents and Chemotherapy* 357–358, Feb. 1976.

Marino et al, "Electrochemical Properties of Silver–Nylon Fabrics," *J. of the Electrochem. Soc.*, 68–72, (Jan. 1985).

Flowers et al., "Efficacy of an Attachable Subcutaneous Cuff for the Prevention of Intravascular Catheter-Related Infection," 261 *Journal of the American Medical Association* 878–883, Feb. 10, 1988.

Maki et al., "An Attachable Silver-Impregnated Cuff for Prevention of Infection with Central Venous Catheter: A Prospective Randomized Multicenter Trial," 85 *The American Journal of Medicine* 307–314, Sep. 1988.

Commercial for VitaCuff®, in publication since approx. 1988.

Anwar & Costerton, "Effective Use of Antibiotics in the Treatment of Biofilm-Associated Infections," 58/12 ASM News 665–68 (Dec., 1992) [See Esp. Fox Inset at 667].

Armstrong Letter "Electric Fields (Biofilm Killing)," 59/6 ASM News 270–71 (Jun., 1993).

*Primary Examiner*—Corrine Maglione
*Attorney, Agent, or Firm*—Arnold, White & Durkee

[57] ABSTRACT

Techniques and apparatus are described for applying alternating and/or pulsed, electrical charges to open circuitry incorporated into medical devices intended to be placed into contact with portions of the body. A catheter assembly is described which comprises a catheter tube, an exterior portion of which is circumferentially surrounded by at least two parallel elongated helical conductive elements which may be operably connected to a power source to create a open circuit to induce an antimicrobial effect in the area proximate the exterior conductive elements through oligodynamic activity. In another embodiment, an oligodynamic dressing is described which incorporates open circuitry which is presented to contact a subject wound.

4 Claims, 3 Drawing Sheets

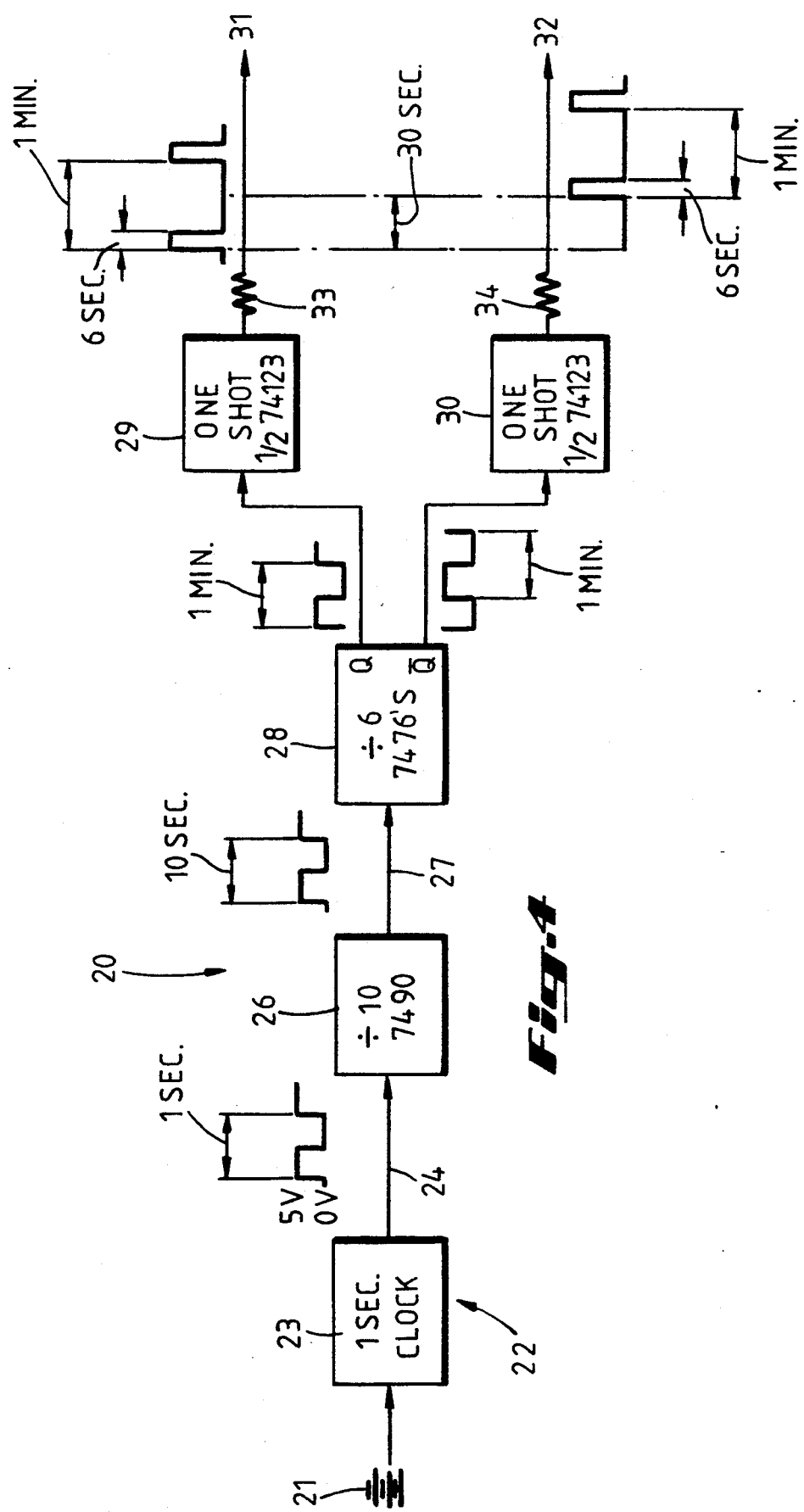

ANTIMICROBIAL CATHETER

This is a continuation-in-part of U.S. patent application No. 07/956,642, filed Oct. 2, 1992 now U.S. Pat. No. 5,324,275 and which is incorporated herein by reference.

FIELD OF THE INVENTION

This present invention relates to antimicrobial devices. More specifically this invention relates to antimicrobial me dical devices employing oligodynamic action.

BACKGROUND OF THE INVENTION

A general difficulty with medical devices which come into contact with infection-sensitive areas of the body is that they may, themselves, introduce infection into the body or serve as a conduit for the introduction of infection over time. These infection-sensitive areas include body orifices and wounds. Intrusive medical devices such as central venous catheters (CVCs), urinary catheters and endotracheal catheters may introduce infection into hospitalized patients when used since the devices are subject to microbial colonization.

The most common organisms causing these infectious complications are *Staphylococcus epidermidis* and *Staphylococcus aureus*. In the case of vascular catheters, these two organisms account for almost 70-80% of all infectious organisms, with *Staphylococcus epidermidis* being the most common organism. *Candida albicans*, a fungal agent, account for about 10-15% of catheter infections. A number of studies have revealed that organisms such as *Staphylococcus epidermidis* send projections into small defects in the polypropylene material, which is used in catheters. Protection against infection is desirable at and around the catheter insertion point to limit entrance of organisms into the intercutaneous tunnel.

A related problem lies within non-intrusive external medical aids such as bandages, gauze pads and other dressings that are placed in contact with wounds on the body during healing. These dressings must be changed regularly and/or have antibiotic medications added to them to resist infection of the wound. In many cases in which the patient's tissue is extremely sensitive, such as wound dressings for burns or ulcers, it would be advantageous to avoid the many changes. Even with frequent and regular dressing changes, a large number of site infections can be expected to occur.

The use of antimicrobial creams or other coatings, such as chlorhexidine, may not provide an effective countermeasure to catheter-related or dressing-related infections. The coatings may themselves be contaminated or be improperly or incompletely applied over the surface of the item rendering the coating ineffective. In addition, the antimicrobial effect: of these coatings is only temporary and has the potential to build resistance by the microbes to the particular antimicrobial agent used.

Heavy metals, particularly gold, silver, and copper are known to exert, in the form of metal ions, an antimicrobial effect known as oligodynamic activity to counter infections. A number of devices have been created which employ such materials to obtain an antimicrobial effect.

A cuff has been designed which is composed of collagen impregnated with silver ions, which may be placed around a central venous catheter prior to catheter insertion and positioned subcutaneously after catheter placement. The collagen induces tissue ingrowth which seals the catheter track, and the antimicrobial activity of the silver serves as an additional barrier to organisms migrating into the catheter track. Due to the collagen composition, the cuff itself actually dissolves away after a short period of time.

A urinary catheter device is also known which includes electrodes originating at the proximal end of the catheter and running along the internal length of the catheter lumen to the catheter's distal end. The catheter is adapted to accommodate current from a constant current source and transmit the current to the internal electrodes. In one embodiment, the electrodes may exit the tubular wall of the catheter near a distal end collection orifice thus exposing their surfaces to the inner lumen of the catheter. The electrodes are preferably made of a heavy metal and are ionized by the constant current source to provide for antimicrobial action.

Another bacterial barrier is known which may be used with indwelling catheters and similar medical devices which is designed to produce a circumferential zone of bacterial inhibition just within the body opening when the device is installed. The barrier is in the form of a fixed or detachable thin band, stretchable or shrinkable ring, or plastic nonconductive tape having a continuous strip of oligodynamic metal, such as silver, zinc, copper or aluminum; a more noble metal, such as platinum or gold; and a self contained current source.

SUMMARY OF THE INVENTION

The invention encompasses techniques and apparatus for applying alternating and/or pulsed, electrical charges to open circuitry incorporated into medical devices intended to be placed in contact with infection-sensitive portions of the body. It therefore offers potentially wide-ranging applications. In one preferred embodiment, an exemplary catheter assembly is described which comprises an intravenous, urinary or endotracheal type catheter having a distal end for insertion into the pertinent area of the body. A central exterior portion of the catheter is circumferentially surrounded by at least two parallel helical conductive elements which are operably connected to a power source capable of energizing the exterior conductive elements to create an open circuit and induce oligodynamic activity in the area proximate the elements. As a result of the helical structure of the conductive elements, the antimicrobial effect is induced within sequential fields of oligodynamic activity along any longitudinal radial segment of the catheter tube.

In another preferred embodiment, an oligodynamic dressing is described in which gauze, or other fabric, incorporates open circuitry which is presented to contact a subject wound.

The open circuitry for each of these exemplary embodiments is adapted to prolong antimicrobial activity through periodically alternating and/or pulsed polarity charge applications. It is highly preferred that the application of this periodic charging occurs after a desired level of antimicrobial activity has been achieved using a constant current source. Testing has shown the use of this type of charge application to significantly prolong the antimicrobial activity provided by the open circuitry.

BRIEF DESCRIPTION OF THE DRAWINGS

FIG. 4 shows an exemplary embodiment of an arrangement useful for providing alternating and/or pulsed charging to the conductive elements of an open circuit.

DETAILED DESCRIPTION OF PREFERRED EMBODIMENTS

In accordance with the present invention, apparatus and methods are described for providing prolonged, effective oligodynamic antibacterial activity in association with a number of medical devices. The invention is illustrated using exemplary embodiments. The techniques and apparatus described and claimed, however, have application to any number of alternative medical devices suitable for use with infection-sensitive areas of the body. Numerous tests have shown the methods and apparatus encompassed by the invention to be highly effective.

It is observed at the outset that a number of types of catheters may be used in constructing catheter assemblies in accordance with the present invention. Among these are central venous catheters (CVCs), urinary catheters and endotracheal catheters.

Figure 1:
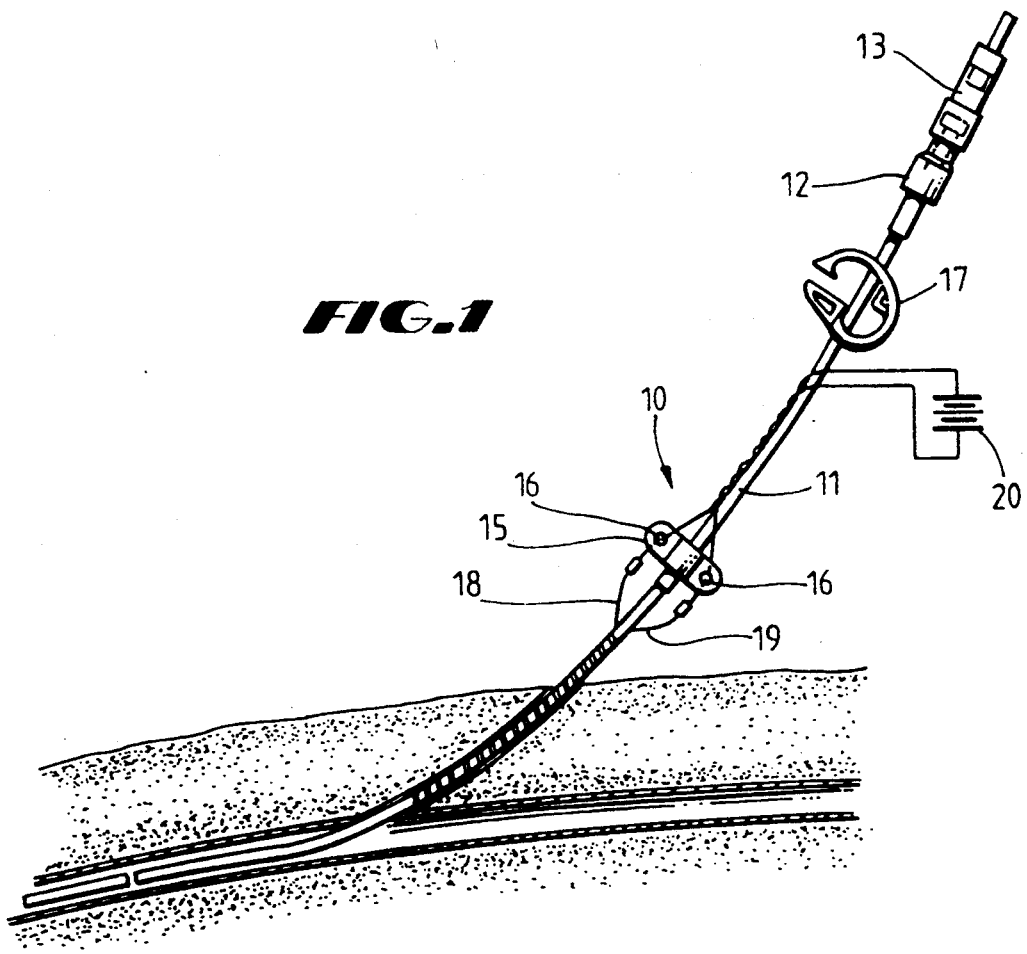
FIG. 1 shows an exemplary catheter assembly 10 constructed in accordance with the present invention.

Referring now to FIG. 1 there is shown an exemplary catheter assembly 10 of the CVC type comprising a catheter tube 11 of the type well known in the art. The proximal end of the catheter tube 11 terminates in a hub 12. Hub 12 typically comprises a controllable orifice useful for the introduction and removal of fluids through the catheter tube 11. Normally, hub 12 is be fitted with a removable cap 13 to provide for added sanitary conditions. The use of such caps is common in the art to prevent contamination of the interior portions of hub 12 when the cap 13 is in place.

Elongated conductive elements 18 and 19 are disposed so as to helically surround a central exterior portion of suction tube 11. As may be seen in FIGS. 1 and 2, elements 18 and 19 should be substantially parallel to each other and in a spaced relation to each other such that the elements do not cross or touch one another at any point along their lengths. Optimal spacing between elements 18 and 19 should be 1 cm or less. Both conductive elements 18 and 19 should be substantially comprised of a material which is electrically conductive and has good oligodynamic properties. Heavy metals, including gold, silver, platinum, iron, aluminum, zinc and copper are recommended. Copper is particularly preferred because of its combination of affordability, ductility, and demonstrated antimicrobial effectiveness.

Figure 2:
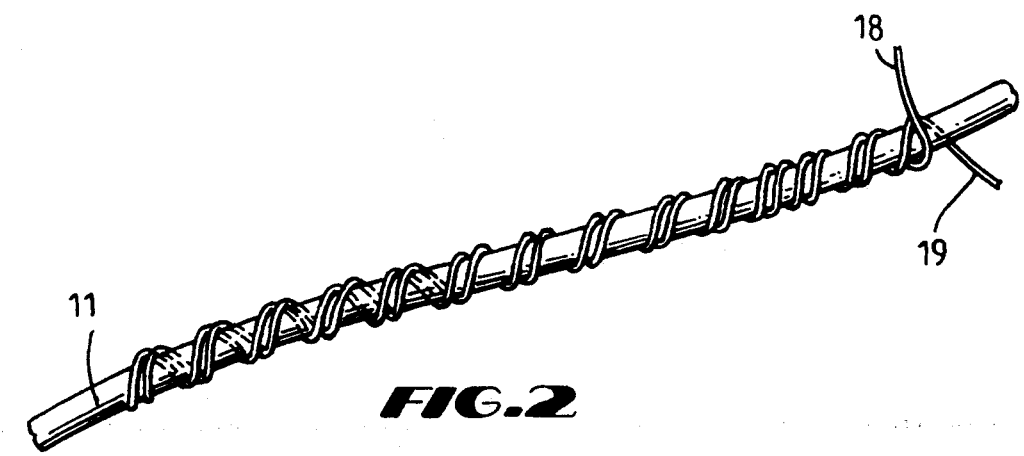
FIG. 2 details an exemplary external placement arrangement for elongated helical elements around portions of the circumference of a catheter assembly.

As is best shown in FIG. 2, elements 18 and 19 may comprise thin wires formed of one of these materials and wound in a helical fashion around a central portion of suction tube 11. In an alternative embodiment, elements 18 and 19 may comprise substrate-type metal layers which have been deposited on the surface of the suction tube 11.

Preferably elements 18 and 19 are fixedly disposed upon the exterior surface of catheter tube 11 to ensure that these elements are not shifted along catheter tube 11 during placement or removal of the catheter assembly 10. If elements 18 and 19 comprise wires, fixed disposition may be accomplished by partially embedding the wires within the surface of the catheter tube 11 such that portions of the elements remain exposed to the exterior environment.

Toward their proximal ends, elements 18 and 19 are operably connected to a power source 20. Preferably, such operable connection is also reversible so that the power source 20 may be disconnected when not in use. Power source 20 comprises an arrangement suitable for periodically applying a predetermined amount of charge to elements 18 and 19. In one preferred embodiment, an alternating charge is applied to the elements 18 and 19 such that the polarity of the charge imparted to each element is periodically reversed from positively-charged to negatively-charged and vice-versa. The charges of successive periods imparted to the elements are of opposite polarity. In a further preferred embodiment, the power source 20 provides a pulsed charge such that a charge of limited duration is periodically imparted to the elements 18 and 19 periodically. Power source 20 may also provide a charge which is both alternating and pulsed.

It is strongly recommended that the alternating and/or pulsating periodic charging not be applied until a desired level of antimicrobial activity is achieved using constant current charging. Constant current charging may be achieved by use of a constant current source such as a battery.

A suitable arrangement for power source 20 is illustrated in FIG. 4 and comprises a current source 21 with associated periodic charging circuitry 22. The current source 21 may be a battery. The charging circuitry 22 of FIG. 4 presents an exemplary construction of such a circuit. Those skilled in the art will appreciate that numerous alternative circuit arrangements are possible which will achieve similar desired results. As shown, clock 23 provides a 5V square wave output 24 having a period of 1 second. The clock output 24 is then fed into a divide-by-ten circuit 26 to produce an output 27 of 10 second duration. Dividing circuits of this nature are known and include commercially available components such as the 7490 integrated circuit from Texas Instruments of Dallas, Tex. Output 27 is then input into a further divider circuit 28 which will divide by 3 and the 2 to produce outputs Q and $\overline{Q}$ each having a complimentary square wave production period of 60 seconds. Q and $\overline{Q}$ are each input into a one-shots 29, 30 adapted to produce a periodic positive charging pulse. An exemplary commercial component suitable for divider circuit 28 would be a 7476 integrated circuit wired to divide by 3 and then by 2; an exemplary commercial component for uses as one-shots 29 and 30 includes a 74123 integrated circuit adapted to produce a positive pulse every 30 seconds. One-shots 29 and 30 will transmit charging outputs 31, 32 to conductive elements 18 and 19. By virtue of these charging outputs, element 18 will be positively-charged with respect to element 19 for six seconds per minute, and element 19 will be positively-charged with respect to element 18 for six seconds per minute. Selected resistors 33 and 34 may be used to assist in regulation of the charging outputs.

When power source 20 is operably connected to elements 18 and 19 and charge is provided to the elements, element 18 is in contact with, for example, the positive terminal of power source 20 to become positively charged. Element 19 would be in contact with the negative terminal of power source 20 to become negatively charged. Since elements 18 and 19 do not contact each other, an incomplete or open circuit is created. When those portions of catheter assembly 10 come into contact with an electrolyte-containing fluid, such as the bodily fluid or moisture of a patient's body, the circuit is completed to a degree. Oligodynamic activity results from the transfer of ions between elements 18 and 19 through this fluid. The oligodynamic activity induces a concomitant antimicrobial effect proximate the area between elements 18 and 19. As a result of the helical structure of the elements 18 and 19 the antimicrobial effect is induced within sequential fields of oligodynamic activity along any longitudinal radial segment of the catheter tube. The oligodynamic effect of the open circuit may be substantially prolonged by the use of alternating and/or pulsed charging of the elements 18 and 19.

It is submitted that the use of a helical structure for elements 18 and 19 provides for a large amount of surface area of the elements to be placed in contact with surrounding electrolyte-containing fluid per unit length of catheter. Periodic reversal of the polarity of charging to the conductive elements 18 and 19 is considered to effectively double the useful lifetime of the elements 18 and 20 while essentially maintaining a constant rate of ion production. Periodic refresh-type pulsing of the charge applied to the elements 18 and 19 is considered to be effective to maintain an established toxic concentration of metallic ions within a surrounding electrolyte-containing fluid.

Using Faraday's Laws of electrolysis, one may calculate the amounts of metallic ions released in relation to the amounts of electric charge provided. The variables dictating the amount of ions released and the length of time over which release will occur include the thickness and length of the conductive elements used and the intensity of the charges provided by the power source.

Figure 3:
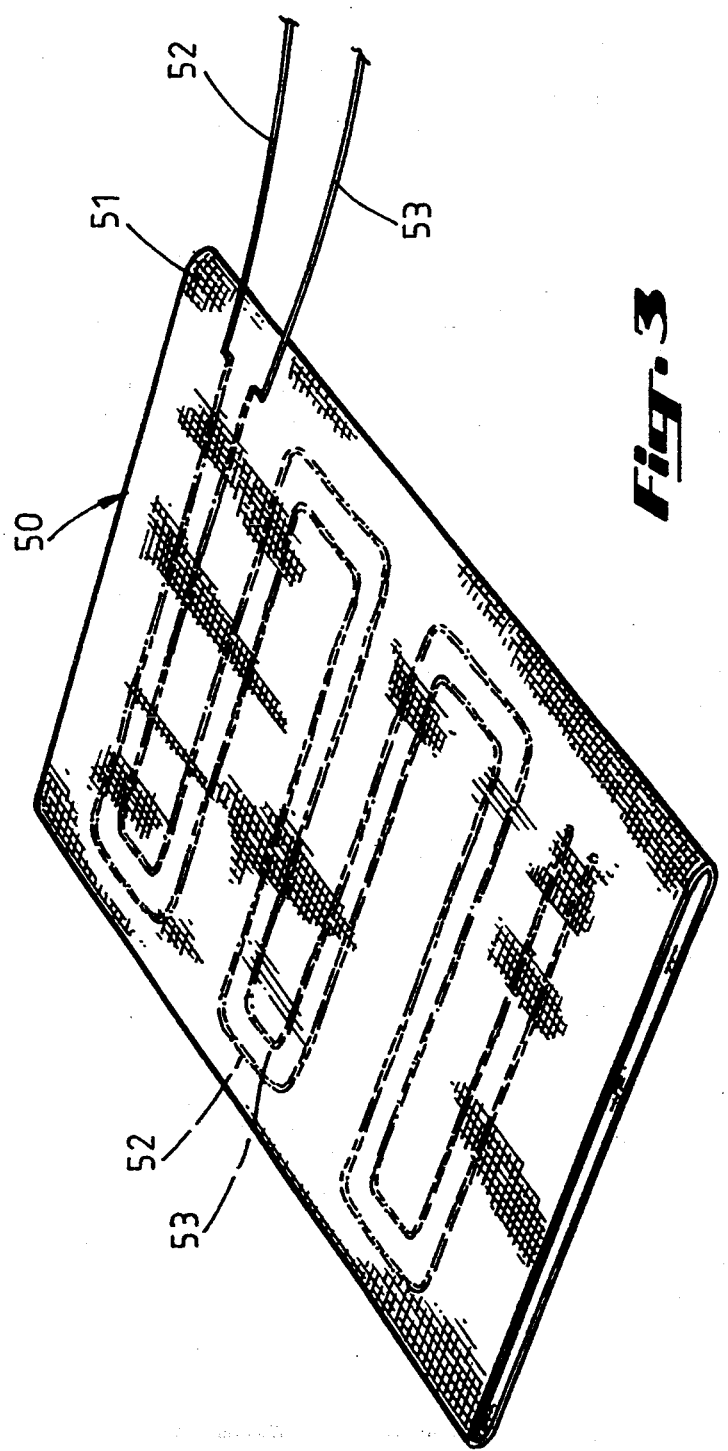
FIG. 3 shows an exemplary dressing 50 in accordance with the present invention.

Turning now to FIG. 3, a dressing 50 is shown which is adapted to be placed over or contact an external wound as that wound is healing. A fabric portion 51 is presented which may be a portion of a bandage, gauze pad or other typical dressing. In an alternative embodiment, fabric portion 51 may be a section of hydrogel dressing or other material adapted to contact a wound. Incorporated into fabric portion 51 are elongated, conductive elements 52 and 53 which may be of a similar composition of those used with catheter assembly 10. The conductive elements 52 and 53 may be woven into fabric portion 51 or otherwise attached such that portions of each come into contact with or are positioned proximate the subject wound as the dressing 50 is placed onto the wound. The elements 52 and 53 should be arranged so that they are proximate and substantially parallel to one another but do not cross or contact the other. A preferred distance is approximately 1 cm or less. However, any distance suitable to permit the creation of an open circuit as described previously is acceptable. Any number of conductive elements 52 and 53 may be arranged in a parallel relationship within fabric section 51.

A power source is operably connected to conductive elements 52 and 53. As with the previously described embodiment of the exemplary catheter 10, the operable connection is also preferably reversible so that the power source may be disconnected when not in use. The power source should be of a type similar to the previously described power source 20 such that it is suitable to provide an alternating charge to elements 52 and 53. An alternating periodic charge may be applied wherein the polarity of the charge imparted to each of these elements is periodically reversed from positively charged to negatively charged and vice versa. In a further preferred embodiment, the power source provides a pulsed charge such that a predetermined amount of charge is imparted to the elements 52 and 53 on a periodic basis. In addition, the periodic charges to elements 52 and 53 may be both pulsed and alternating.

A number of comparative in vitro and in vivo tests have demonstrated the antimicrobial efficacy of oligodynamic catheter assemblies constructed and operated in accordance with exemplary catheter assembly 10 the present invention.

EXAMPLE 1

An in vitro test model simulating an indwelling CVC was made from two petri dishes whose interior portions were connected by a narrow plastic tunnel. The first petri dish (dish A) represented a contaminated external environment. The second petri dish (dish B) simulated the intravascular area into which the tip of a CVC would penetrate. The tunnel represented the intercutaneous portion of a catheter wound leading from the external environment to the intravascular area. A sterile CVC-type catheter was capped at its proximal end and placed into the dishes such that the proximal portion was resting in dish A. The central portion of the catheter was passed through the plastic tunnel until the distal portion of the catheter rested in dish B.

Prior to placement into the dishes, the catheter had been prepared such that a pair of narrow gage silver wires were disposed helically in a parallel relation to each other along the central length of the catheter. Toward the proximal end of the catheter, portions of these wires had been encased in a plastic covering to prevent contact between the wires. The plastic covering had been stripped from distal portions of both wires beginning at a point inside of dish A which corresponded to a point just outside the catheter wound. The stripped sections of the wires had been wound helically around several inches of the catheter's central portion. During preparation, care was taken to ensure that the stripped wire sections did not touch one another. The proximal ends of the wires were connected to a power source.

A control model was included in the tests which employed an uncoated catheter with no conductive elements arranged in petri dishes in the same manner as the catheter of the in vitro model.

To simulate a contaminated environment, a 50 ml solution of saline/broth was added to petri dish A and an equal amount was added to dish B. 0.1 ml of $2 \times 10^5$ CFU/ml of Staphylococcus epidermidis was added to dish A. With the control model, growth of Staphyloccus epidermidis (in excess of 1000 CFU) in petri dish B and proximate the distal portion of the catheter was generally observable within 24 hours absent conductive elements and electrical charging.

Testing repeatedly showed that, upon application of a continuous, low current of 20 micro amperes provided by the power source, growth of the organism was not observed in dish B for at least seven days. Over 50 tests were performed using this model. Different organisms were used including S. epidermidis, S. aureus, gram negative organisms and Candida species. In all of the experiments, the distal portion of the catheter remained sterile for seven days during which no culture growth occurred in dish B. In a control model, however, the distal portion of the control catheter in dish B was colonized with >$10^3$ colonies within 24 hours of placement of the organism into dish A.

Experimentation illustrates the efficacy of using alternating, pulsed charging to prolong the antimicrobial effects of an oligodynamic catheter assembly. Use of a thin silver wire of 0.1 mm diameter with a length of 5 cm and a continuous charging current of 20 micro amperes typically results in depletion of silver ions to the point where antimicrobial activity ceases within five to seven days. However, by reversing the polarity of the charging current every 24 hours, the antimicrobial effect was extended to eleven days.

EXAMPLE 2

Use of alternating polarity charges which were pulsed produced even better results. In these experiments, 20 micro amperes of charge were provided to silver wires of the same type as used in the other tests, but for only six seconds out of every thirty seconds. The polarity of the charges applied to the elements was reversed every 24 hours. In these tests, antimicrobial activity continued for at least 30 days. After 30 days there was microbial contamination in dish B but no growth of *S. epidermidis*.

EXAMPLE 3

Further in vitro testing has indicated that zones of microbial inhibition of catheter assemblies constructed in accordance with the present invention are significantly greater than that achievable with conventional catheters coated with antimicrobial agents even over the long term.

In general, a greater zone of inhibition translates into greater clinical efficacy in the reduction of antimicrobial infection. A system for measuring the degrees of effectiveness associated with various sized zones of inhibitions was discussed in Sherertz et al., *Journal of Infectious Diseases* 167:98-106, 1993. According to that model, devices having zones of inhibition of 0–10 mm exhibit little or no clinical antimicrobial efficacy. Zones of 10–15 mm translate into moderate clinical efficacy while zones greater than 15 mm translate into high efficacy.

In petri agar dishes, zones of inhibition against microorganisms were measured perpendicular to the longitudinal axis of the applied catheter tube. Resistance to three types of organisms was tested, and the test with respect to each organism was repeated three times. The tests compared the relative sizes of inhibition zones for Arrow Biogard type catheters and oligodynamic catheters constructed similar to those in Examples 1 and 2 but using only 10 microamperes of current. Control catheters, which incorporated no coatings or other antimicrobial measures were also included.

The following table illustrates comparative data using the Sherertz model:

|  | Zone of Inhibition (Diameter in mm) |
|---|---|
|  | *S. epidermidis* |
| Control (uncoated) catheters | 0 |
| Arrow Biogard catheter (coated with chorhexidine and silver sulfadiazine) | 14 |
| Oligodynamic catheter (using 10 microamperes of current) | 15 |
| Oligodynamic catheter (using 10 microamperes of current pulsed for 12 seconds/min. and alternative polarity) | 13 |
|  | *Candids albicans* |
| Control (uncoated) catheters | 0 |
| Arrow Biogard catheter | 9 |
| Oligodynamic catheter (using 10 microamperes of continuous curent) | 13 |
|  | *S. aureus* |
| Control (uncoated) catheters | 0 |
| Arrow Biogard catheter | 13 |
| Oligodynamic catheter (using 10 microamperes of continous current) | 18 |

EXAMPLE 4

In vivo experiments have also demonstrated the effectiveness of oligodynamic catheters which utilize an alternating and pulsating current. An established rabbit model (Shererty et al., *Journal of Infectious Diseases* 167:98-106, 1993) was used wherein the three types of catheters (control, Arrow Biogard and an oligodynamic catheter constructed in accordance with the present invention) were percutaneously inserted in rabbits. Immediately after insertion, each catheter insertion site was inoculated with 0.1 ml of $10^5$ CFU of *S. aureus* from the bloodstream of a patient with catheter-related *S. aureus* bacteremia. Seven days after insertion, the catheters were removed. The subcutaneous (SQ) catheter segment and the tips of the catheters were then cultured by quantitative catheter cultures. The following results were obtained where the catheters were cultured by the standard semi-quantitative roll-plate culture and sonication methods:

| Animal Number | Catheter Number | Catheter Type | Number of colonies per catheter segment | |
|---|---|---|---|---|
|  |  |  | Tip | SQ |
| 225 | 1 | control | 98 | 110 |
|  | 2 | control | 7 | 6 |
|  | 3 | oligodynamic | 0 | 0 |
|  | 4 | oligodynamic | 2 | 0 |
| 227 | 5 | control | 10 | 15 |
|  | 6 | control | >1000 | >1000 |
|  | 7 | oligodynamic | 0 | 0 |
|  | 8 | oligodynamic | 1 | 0 |
| 230 | 9 | control | 29 | 135 |
|  | 10 | control | 0 | 6 |
|  | 11 | oligodynamic | 0 | 0 |
|  | 12 | oligodynamic | 0 | 0 |
| 232 | 13 | control | >1000 | >1000 |
|  | 14 | control | 93 | >1000 |
|  | 15 | oligodynamic | 0 | 0 |
|  | 16 | oligodynamic | 0 | 0 |
|  | 17 | Arrow Biogard | >1000 | >1000 |
|  | 18 | Arrow Biogard | 0 | 0 |
|  | 19 | Arrow Biogard | 2 | 8 |

The oligodynamic catheters used in animals 225, 227, 230 and 232 incorporated external elongated helical conductive elements which were connected to a 0.6 volt small battery power source. The continuous charging current was roughly 10–15 microamperes.

The efficacy of the continuous charging oligodynamic catheter was achievable using alternating and/or pulsating; charges. Comparative testing was conducted in rabbits wherein a 20 microampere charging current for an oligodynamic catheter was pulsed by charging for 12 seconds out of every 60 seconds. Cultures were collected using the roll plate semiquantitative method described in Maki et al., "A Semiquantitative Culture Method for Identifying Intraveous Catheter-Related Infections," 296 N. Engl. J. Med. 1305-09 (1977) and the sonication method discussed in Sherertz et al., "Three-Year Experience with Sonicated Vascular Catheter Culture in a Clinical Microbiology Laboratory," 28 J. Clin. Microbiol. 76-82 (1990). The polarity of the charging current to the conductive elements was alternated every 24 hours.

| Catheter Number | Catheter Type | Number of colonies cultured by | | | |
|---|---|---|---|---|---|
| | | Roll plate semiquantitative method from | | Sonication method from | |
| | | Tip | Subcutaneous Segment | Tip | Subcutaneous Segment |
| 1 | Control | >1000 | >1000 | >1000 | >1000 |
| 2 | Control | >1000 | >1000 | >1000 | >1000 |
| 3 | Control | >1000 | >1000 | >1000 | >1000 |
| 4 | Control | >1000 | >1000 | >1000 | >1000 |
| 5 | Arrow Biogard | >1000 | >1000 | 180 | >1000 |
| 6 | Arrow Biogard | 1 | 16 | 0 | 20 |
| 7 | Oligodynamic | 0 | 0 | 0 | 0 |

Histopathologic studies on the subcutaneous soft tissue area near the catheter insertion points showed no evidence of any thermal injury or frictional irritation from use of the oligodynamic catheter versus a control catheter. However, purulence was noted at the insertion site of the control catheters.

EXAMPLE 5

An oligodynamic catheter was also, implanted in a patient at the Texas Medical Center in Houston. The device was used as a cystostomy bladder catheter and was operated at a continuous current of 20 microamperes. The device remained in place for three weeks without any symptoms or signs of discomfort.

Those skilled in the art will recognize that, while specific embodiments have been illustrated and described, various modifications and changes may be made without departing from the spirit and scope of the invention.

What is claimed is:

1. A catheter comprising:
   (a) a catheter tube having a proximal end and a distal end and adapted to transmit fluid therethrough;
   (b) a hub at the proximal end of said catheter tube to permit fluid flow through said catheter tube;
   (c) at least two elongated external conductive elements composed of oligodynamic metals fixedly disposed in a substantially parallel spaced relation to each other and to helically surround the exterior circumference of a central portion of said catheter tube, said elements forming portions of an open circuit upon application of a power source; and
   (d) a power source operably connected to said external conductive elements so as to periodically apply current for several seconds to one conductive element or the other.

2. The catheter assembly of claim 1, wherein the current of successive periods are opposite in polarity.

3. The catheter assembly of claim 1, wherein the currents are of limited duration.

4. The catheter assembly of claim 1, wherein the currents of successive periods are of limited duration and opposite in polarity.

* * * * *